United States Patent [19]

Bockrath

[11] 4,215,227

[45] Jul. 29, 1980

[54] RECOVERY OF PARA-NITROSODIUM PHENOLATE

[75] Inventor: Richard E. Bockrath, Wilmington, Del.

[73] Assignee: E. I. Du Pont de Nemours and Company, Wilmington, Del.

[21] Appl. No.: 955,505

[22] Filed: Oct. 27, 1978

[51] Int. Cl.[2] .............................................. C07C 79/26

[52] U.S. Cl. .................................... 568/706; 568/708

[58] Field of Search ................ 568/708, 706, 749, 709

[56] References Cited

U.S. PATENT DOCUMENTS

| | | | |
|---|---|---|---|
| 2,275,045 | 3/1942 | Gebe | 568/749 |
| 2,407,045 | 9/1946 | Tyrer | 568/706 |
| 2,743,301 | 4/1956 | Melucci | 568/706 |
| 3,280,407 | 11/1966 | Cox | 568/706 |
| 3,506,724 | 4/1970 | Tuemmler et al. | 568/706 |
| 3,624,164 | 11/1971 | Georgiou | 568/706 |
| 3,708,545 | 1/1973 | Squire | 568/706 |
| 3,804,907 | 4/1974 | Kablaoui | 568/706 |

OTHER PUBLICATIONS

Korenman et al., "Journal of Applied Chemistry", 50 No. 9, pp. 1969–1971, Sep. 1977.

"Russian Journal of Physical Chemistry" 45, (4), 1971.

*Primary Examiner*—Werren B. Lone

[57] ABSTRACT

A process for preparing alkali metal salts of para-nitrophenol by contacting para-chloronitrobenzene with an aqueous solution of (1) aqueous caustic and (2) recycled filtrate and washing solution from the preparation of para-nitrophenol containing 5–20% by weight of said alkali metal salts at a temperature of from 180°–250° C. and at autogenous pressure in 30 seconds to 10 minutes with the mole ratio of caustic to chloronitrobenzene of from 2:1–4:1, caustic concentration in the aqueous solution of from 5–20%, the amount of recycle ranging from 5–45% by weight based on the aqueous solution.

6 Claims, No Drawings

RECOVERY OF PARA-NITROSODIUM PHENOLATE

DESCRIPTION

TECHNICAL FIELD

The present invention relates to recovering alkali metal salts of para-nitrophenol in a high quality form. More specifically, the present invention relates to a process for preparing an alkali metal salt of para-nitrophenol from para-chloronitrobenzene and an aqueous caustic solution after incorporating, with said salt and caustic, residual solutions from the preparation of said salts.

BACKGROUND ART

U.S. Pat. No. 3,624,164 discloses a continuous process for the preparation of alkali metal salts of nitrophenols by contacting a chloronitrobenzene with aqueous caustic at 180°-250° C. at autogenous pressure for 30 seconds to 10 minutes at a mole ratio of caustic to chloronitrobenzene of at least 2.0 and a power input into the feed streams of the reaction of at least 2.3 horsepower per 1,000 gallons of reaction volume. However, the aqueous solutions remaining after the removal of product therefrom contain a significant amount of product in the form of fines and soluble material that unless subjected to some recovery technique would be lost.

Other processes involving the preparation of a nitrophenol are disclosed in U.S. Pat. Nos. 3,283,011; 3,506,724; 3,804,907; 3,708,545 and 2,407,045.

U.S. Pat. No. 2,275,045 discloses a method for recovering phenolic compounds from aqueous solutions of the corresponding calcium phenolates by heating with water at elevated temperatures and under superatmospheric pressure to form calcium hydroxide and the free phenolic compound.

U.S. Pat. No. 2,743,301 discloses a method for separating the ortho- and para-isomers of alkali metal nitrophenates by adjusting the solution containing both to a low percentage of weight of both sodium hydroxide and sodium chloride and then maintaining the temperature at 35°-55° C. to precipitate the p-isomer.

The salting out of nitrophenols from aqueous solutions is disclosed in Journal of Applied Chemistry, USSR v. 50(9) 1977 by Korenman, Bortnikova and Nefedova.

The Effect of Salts in the Activity of p-Nitrophenol and its Anion in Aqueous Solution is the title of an article disclosed in the Russian Journal of Physical Chemistry, 45(4), 1971 by Sumskayn, Bugaevskii and Chernukha.

DISCLOSURE OF THE INVENTION

Now a process has been found whereby alkali metal salts of p-nitrophenol can be recovered in the form of a high quality product with reduced water insolubles and calcium ion.

Accordingly, a process has been found for recovering alkali metal salts of para-nitrophenol with reduced water insolubles and calcium ion, said process comprising contacting (1) a feed stream of parachloronitrobenzene, (2) a residual aqueous solution, from the preparation of alkali metal salts of paranitrophenol by the procedure described herein, containing less than 20% by weight of said alkali metal salts and (3) a feed stream of aqueous caustic solution selected from the group consisting of sodium hydroxide and potassium hydroxide at a temperature of from 180°-250° C. and at autogeneous pressure in a time interval of from 30 seconds to 10 minutes at a mole ratio of caustic to chloronitrobenzene of 2:1-4:1, preferably 2:1-2.8:1, the caustic concentration in said aqueous solutions being maintained at from 5-20% and at a power input into the feed streams of the reaction system of at least 2.3 horsepower per 1,000 gallons of reaction volume.

The process of this invention is an improvement, in the process for preparing alkali metal salts of p-nitrophenol according to the aforesaid basic process, whereby residual aqueous solutions from the preparation of alkali metal salts of p-nitrophenol are recycled back to the reaction with fresh caustic and chloronitrobenzene for the purpose of recovering said salts that are present in the residual aqueous solutions in the form of high quality product.

If one were to recover the alkali metal salts of p-nitrophenol from the residual aqueous solutions from the preparation of said salts merely by treating the aqueous solutions therefrom separately, the recovered salts would be high in water insolubles and calcium ion and therefore of poor quality. However, quite surprisingly, when the residual aqueous solutions from the preparation of said salts are subjected to the process of the present invention, the recovered salts are higher quality with lower water insolubles and calcium ion.

The residual aqueous solutions containing alkali metal salts of p-nitrophenol are also referred to herein as combined solution from filtration and washings from the process of preparing said salts by a process involving the reaction of caustic and chloronitrobenzene. The process for the preparation of alkali metal salts of p-nitrophenol is disclosed in U.S. Pat. No. 3,624,164 which is hereby incorporated by reference. The residual aqueous solutions from the aforesaid process contain fines and soluble product that is carried through with aqueous solutions from the separation steps and washing steps. The amount of alkali metal salt soluble product in the combined aqueous solutions remaining after product separation is less than 20% by weight, generally 5-20% by weight. Most often the amount is 5-15% by weight.

The caustic stream can be an aqueous stream of either sodium hydroxide or potassium hydroxide. In order to obtain a high purity nitrophenol product, the concentration of hydroxide in the aqueous solution must be maintained at a level of from 5-20% by weight, preferably 7-13% by weight caustic. The residual aqueous solutions from the preparation of the nitrophenol salt containing dissolved nitrophenol salt and nitrophenol salt fines are used to partially replace water in the makeup of the aqueous caustic solution. Thus, any amount of residual aqueous solutions can be used to attain the above hydroxide levels. Generally, however, the benefits of the present invention extend only to using from 5-55% by weight of the combined filtrate solution and brine washings that are produced by the process for the salt preparation. Preferably 25-45% by weight of the combined filtrate solution and brine washings are used. When more than 55% of the combined filtrate solution and brine washings are used, the quality of the recovered product is lower. The use of less than 5% of said filtrate and washings is not economically justifiable. This amount of the residual aqueous solutions that may be used in the process of the invention based on the total aqueous solutions (aqueous caustic solution and residual aqueous solutions) is 5–45% by weight, preferably 20–40% by weight.

The process of the present invention may be conducted continuously or batchwise. It is preferred that the reaction be conducted continuously.

When the process of the present invention is carried out continuously, separate streams of (1) chloronitrobenzene and (2) aqueous caustic with the combined filtrate and washings are continuously fed into a reactor adapted for continuous operation. An example of such equipment is a pipeline reactor of the type well known to those skilled in the art. In the pipeline reactor, the separate streams of chloronitrobenzene and said aqueous caustic are well mixed in a mixing tee whereby the desired reaction is caused to begin. The pipeline reactor is maintained at a reaction temperature of 180°–250° C. by immersion in a temperature-controlled oil bath, by electric heating or by any other suitable means.

The two streams are brought together at such a rate that the two immiscible phases, the oil chloronitrobenzene phase and the aqueous caustic phase, are well mixed. Since separation of the phases should not occur in the reactor, sufficient turbulence is maintained by controlling the power input on the feed streams to insure intimate contact of the reactants during the passage of the reaction mixture through the reactor. It has been found that the degree of agitation is critical to the continuous production of high purity nitrophenol product. If the power input on the feed streams is less than 2.3 horsepower per 1,000 gallons, conversion rates fall off and the yield of byproduct impurities increases. The preferred range of power input on the feed streams is from 4.4–13.5 horsepower per 1,000 gallons of reaction volume. Normally, power inputs on the feed stream above 17.0 horsepower are unnecessary.

The reaction is carried out in a temperature range of 180°–250° C., preferably 190°–220° C. The reaction time varies from 30 seconds to 10 minutes, preferably 2–8 minutes. The reaction is also carried out under autogenous pressure. At these temperatures, reaction times and pressure, almost complete conversion rates are obtained with only trace amounts of byproducts present in the final product.

The invention is not limited to the exact procedure heretofore described. Variation of the procedure can be made without departing from the scope of the invention. For instance, the mixing and heating may be accomplished in any sequence. Thus, instead of separately preheating the reactants prior to mixing, one reactant, preferably the caustic in this case, may be preheated and mixed with the other reactant in the liquid state. The mixture is then further heated in the reactor. Alternatively, both reactants may be mixed at a relatively low temperature in the liquid state and subsequently brought to reaction temperature.

After the reaction mixture has passed through the reactor, the reaction mass from the reactor is flashed to atmospheric pressure through a let-down valve into a liquid-gas separator where any unreacted chloronitrobenzene is steam distilled off. The aqueous slurry is continuously withdrawn into a receiver and is subsequently cooled to below 60° C. The precipitate consisting of crystalline alkali metal salts of nitrophenol is isolated by filtration in a known manner. The para-alkali metal salt may be recovered directly by any means of filtration.

After the filtration of the alkali metal salt of p-nitrophenol, water, caustic solution or an aqueous solution of an alkali metal salt can be used to wash said salt. The higher solubility of the salt in water makes the aqueous solution of an alkali metal salt the preferred washing solution. The most preferred aqueous solution of an alkali metal salt is sodium chloride. The liquid from filtration and the liquid from washing may be combined and used to recover the nitrophenol salt according to the invention or the liquids can be separately used in the process of the invention.

Processes for the preparation of p-chloronitrobenzene by chlorination of benzene followed by nitration and purification are known in the art and are described, for example, in "Unit Processes in Organic Synthesis", 5th Ed. 1958 by P. H. Groggins.

The following examples further illustrate the invention. All references to parts or percent are by weight unless otherwise indicated.

EXAMPLES

EXAMPLE 1

Best Mode

A. A stream of molten p-chloronitrobenzene preheated to 125° C. and a stream of 10% (by weight) of an aqueous solution of sodium hydroxide preheated to 200°–210° C. were continuously brought together in a mixing tee at a rate of 14.6 parts per minute of p-chloronitrobenzene (PCNB) to 85.4 parts per minute of the caustic (mole ratio of caustic to PCNB of 2.3). The power input on the feed streams totalled 4.2 horsepower per 1,000 gallons of reaction volume. The reaction began when the two streams were brought together in the mixing tee and continued as the mixture transversed an Inconel 600 pipeline reactor. Pressure in the reactor was 350–450 psig. The residence time of the reactants in the reactor was approximately 4–6 minutes. Any unreacted p-chloronitrobenzene was removed by flashing the reaction mass to atmospheric pressure through a let-down valve into a liquid-gas separator. The reaction mass was cooled to 40° C. by flashing to subatmospheric pressure and the yellow crystalline product was isolated as the dihydrate of p-nitrophenol sodium salt from aqueous sodium chloride and caustic soda solution by filtration. p-Chloronitrobenzene conversion was essentially 100%. The yield of isolated product after the product was washed with 7½% by weight NaCl brine (1.3 parts brine per part of product) was 92.3% of theoretical yield. 7.7 Percent of the product was retained in the solution from filtration and washings because of its solubility or as "fines" carry-through. The table below summarizes the product analysis.

B. The above reaction was continued except that the molten p-chloronitrobenzene was mixed with an aqueous solution of sodium hydroxide and recycled combined solution from filtration and brine (NaCl) washings at a ratio of 14.6 parts per minute of p-chloronitrobenzene to 85.4 parts per minute of said aqueous solution. The aqueous solution was prepared by mixing 16.4 parts per minute of 50% aqueous sodium hydroxide with 45.0 parts per minute of water and with 24.0 parts per minute of recycled solution and washings (35% by weight of the combined total filtrate and washings from the process of preparing p-nitrophenol sodium salt or 28% by weight of filtrate and washings based on the aqueous solution). The yield of isolated product after brine washing was 96.8% of theoretical, 3.2% being retained in the filtration because of its solubility or as "fines"

carrythrough. The product thus obtained was analyzed and the data obtained shown below in the table.

COMPARATIVE EXAMPLE A

Part A of Example 1 was repeated and the solution from filtration and washings were combined with purified sodium chloride (99.7+% pure) in the ratio of 11.2 parts purified sodium chloride to 88.8 parts of said solution. The mixture was agitated for 30 minutes while at 40° C. and an additional 1.4 parts of dehydrate of p-nitrophenol sodium salt was recovered upon filtration. Total combined yield from Example 1A and the above was 96.8% of theoretical. The product was analyzed and the data obtained as shown in the table below.

COMPARATIVE EXAMPLE B p-Nitrophenol sodium salt samples from Part A of Example 1 and Comparative Example A were compared to determine differences which could affect final end-use.

Part A of Example 1 was repeated and the sodium salt of the p-nitrophenol product was recovered according to Comparative Example A. The resulting product was mixed with the product obtained from Part A of Example 1 at a ratio 92.3 parts of product from Part A of Example 1 to 4.5 parts of Comparative Example A to form a composite. Table I summarizes the data obtained. Composite material from Part A of Example 1, Comparative Examples A and B were found to contain higher impurity levels than material from Example 1 as is shown in the table.

TABLE I

| Test | Example 1A | Comparative Example A |
|---|---|---|
| Purity | 77.0 | 59.7 |
| Water Insolubles (weight %) | Nil | 0.39 |
| $Ca^{+2}$ion (ppm) | <1 | 390 |
| Emulsion Test (1) | Clear | Emulsion |

| Test | Comparative Example B Example 1A (92.3) and Comparative Example A (4.5) | Example 1 |
|---|---|---|
| Purity | 76.2 | 76.8 |
| Water Insolubles (weight %) | 0.018 | Nil |
| $Ca^{+2}$ion (ppm) | 18 | <1 |
| Emulsion Test (1) | Emulsion | Clear |

(1) 5% solution of product in water (100 ml) mixed with 15 ml of methylchloroform was allowed to stand to observe phase separation. If the organic layer was not clear, an emulsion was present.

EXAMPLE 2 p-Nitrophenol sodium salt is a useful intermediate in the production of various insecticides such as o,o-dimethyl-o-p-nitrophenyl-phosphorothioate. p-Nitrophenol sodium salt samples from Example 1 and Part A of Example 1, Comparative Examples A and B above were used in the preparation of o,o-dimethyl-o-p-nitrophenyl-phosphorothioate using the process described in U.S. Pat. No. 3,590,104 (Example 1).

The process consists of a partial dehydration of p-nitrophenol sodium salt hydrate using toluene as the azeotroping solvent. The remaining water is removed during the reaction with o,o-dimethylchlorophosphorothioate by additional refluxing. The crude product is purified by successive washing with water, a 3% sodium carbonate solution, 10% sulfuric acid and finally water. The phosphorothioate produced from the p-nitrophenol sodium salt in Examples 1A and 1B were processed without difficulty giving product of comparable yield and color. However, when p-nitrophenol sodium salt from Comparative Example A and Comparative Example B was used, they formed a stable emulsion in the water washing step and could not therefore be processed further to form the purified phosphorothioate.

INDUSTRIAL APPLICABILITY

Alkali metal salts of p-nitrophenol are useful intermediates in the synthesis of many organic compounds, e.g., insecticides.

I claim:

1. In the process for preparing alkali metal salts of para-nitrophenol by contacting (1) a feed stream of para-chloronitrobenzene and (2) a feed stream of aqueous caustic solution selected from the group consisting of sodium hydroxide and potassium hydroxide at a temperature of from 180°-250° C. and at autogeneous pressure in a time interval of from 30 seconds to 10 minutes at a mole ratio of caustic to chloronitrobenzene of from 2:1-4:1, the caustic concentration in said aqueous solution being maintained at from 5-20% and at a power input into the feed streams of the reaction system of at least 2.3 horsepower per 1,000 gallons of reaction volume, and filtering and washing the alkali metal salt of para-nitrophenol, the improvement wherein from 5-45% by weight, based on the combined aqueous caustic solution, filtrate and washing solution from said process for the preparation of said salts, of the filtrate and washing solution containing from 5-20% by weight based on the solution of alkali metal salts is present in the feed stream of aqueous caustic solution.

2. The improvement of claim 1 wherein 20-40% of the filtrate and washing solution is used.

3. The improvement of claim 1 wherein the mole ratio of caustic to chloronitrobenzene is 2:1-2.8:1.

4. A process for preparing an alkali metal salt of para-nitrophenol with reduced water insolubles and calcium ion, said process comprising contacting (1) a feed stream of para-chloronitrobenzene and (2) an aqueous solution made up of (a) from 5-45% by weight, based on the total aqueous solution, of a combined filtrate and washing solution from the preparation of an alkali metal salt of para-nitrophenol containing less than 20% of alkali metal salt and (b) a feed stream of aqueous caustic solution selected from the group consisting of sodium hydroxide and potassium hydroxide, the caustic concentration in said aqueous solution being from 5-20% by weight, said contacting conducted at a temperature of from 180°-250° C., at autogeneous pressure in a time interval of from 30 seconds to 10 minutes, at a mole ratio of caustic to chloronitrobenzene of from 2:1-4:1, and at a power input into the feed streams of the reaction system of at least 2.3 horsepower per 1,000 gallons of reaction volume.

5. The process of claim 4 wherein 20-40% of the combined filtrate and washings solution are used.

6. The process of claim 4 wherein the mole ratio of caustic to chloronitrobenzene is 2:1-2.8:1.

* * * * *

UNITED STATES PATENT OFFICE
CERTIFICATE OF CORRECTION

PATENT NO. : 4,215,227

DATED : July 29, 1980

INVENTOR(S) : Richard E. Bockrath

It is certified that error appears in the above-identified patent and that said Letters Patent are hereby corrected as shown below:

Column 6, line 32, Claim 1, "," should read --;--.

Column 6, lines 34-36, Claim 1, that portion of the Claim reading "for the preparation of said salts" and "from 5-20% by weight based on the solution of" should be deleted and appear as follows:

--process; of the filtrate and washing solution containing alkali metal salts is present in the feed stream of aqueous caustic solution--.

Signed and Sealed this

*Twenty-eighth* Day of *April 1981*

[SEAL]

*Attest:*

RENE D. TEGTMEYER

*Attesting Officer* *Acting Commissioner of Patents and Trademarks*